(12) United States Patent
Bode

(10) Patent No.: US 11,298,458 B2
(45) Date of Patent: Apr. 12, 2022

(54) DRUG DELIVERY DEVICE

(71) Applicant: SANOFI-AVENTIS DEUTSCHLAND GMBH, Frankfurt am Main (DE)

(72) Inventor: Andreas Bode, Frankfurt am Main (DE)

(73) Assignee: Sanofi-Aventis Deutschland GMBH, Frankfurt am Main (DE)

(*) Notice: Subject to any disclaimer, the term of this patent is extended or adjusted under 35 U.S.C. 154(b) by 960 days.

(21) Appl. No.: 15/760,879

(22) PCT Filed: Sep. 5, 2016

(86) PCT No.: PCT/EP2016/070882
§ 371 (c)(1),
(2) Date: Mar. 16, 2018

(87) PCT Pub. No.: WO2017/045959
PCT Pub. Date: Mar. 23, 2017

(65) Prior Publication Data
US 2019/0083701 A1    Mar. 21, 2019

(30) Foreign Application Priority Data
Sep. 18, 2015 (EP) .................................. 15185785

(51) Int. Cl.
*A61M 5/145* (2006.01)
*A61M 5/24* (2006.01)
*A61M 5/162* (2006.01)

(52) U.S. Cl.
CPC .......... *A61M 5/1454* (2013.01); *A61M 5/145* (2013.01); *A61M 5/1452* (2013.01);
(Continued)

(58) Field of Classification Search
CPC .......... A61M 5/24; A61M 2005/14506; A61M 2005/2433; A61M 5/1454; A61M 5/145;
(Continued)

(56) References Cited

U.S. PATENT DOCUMENTS

| 4,394,863 | A |   | 7/1983 | Bartner |
| 6,053,890 | A | * | 4/2000 | Moreau Defarges ... A61M 5/30 604/232 |

(Continued)

FOREIGN PATENT DOCUMENTS

| GB | 1263355 | 2/1972 |
| GB | 2490807 | 11/2012 |

OTHER PUBLICATIONS

International Search Report and Written Opinion in International Application No. PCT/EP2016/070882, dated Mar. 20, 2017, 8 pages.
(Continued)

*Primary Examiner* — Tiffany Legette
(74) *Attorney, Agent, or Firm* — Fish & Richardson P.C.

(57) ABSTRACT

The present disclosure relates to a drug delivery device for dispensing of a liquid medicament, the device comprising: a housing to accommodate a cartridge filled with the medicament and having a piston slidably displaced inside the cartridge and sealing a proximal end of the cartridge, at least one resilient member having a first end arranged at an inside facing side wall portion of the housing and having a second end (opposite to the first end to abut with the piston of the cartridge.

20 Claims, 3 Drawing Sheets

(52) U.S. Cl.
CPC ............... *A61M 5/24* (2013.01); *A61M 5/162* (2013.01); *A61M 2005/14506* (2013.01); *A61M 2005/2433* (2013.01); *A61M 2205/8206* (2013.01); *A61M 2207/00* (2013.01)

(58) Field of Classification Search
CPC ............... A61M 5/1452; A61M 5/162; A61M 2205/8206
See application file for complete search history.

(56) References Cited

U.S. PATENT DOCUMENTS

2007/0255227 A1* 11/2007 Haase ............... A61M 5/14276
604/218
2015/0320936 A1* 11/2015 Dunne .................. A61M 5/288
604/199

OTHER PUBLICATIONS

International Preliminary Report on Patentability in International Application No. PCT/EP2016/070882, dated Mar. 20, 2018, 6 pages.

* cited by examiner

DRUG DELIVERY DEVICE

CROSS REFERENCE TO RELATED APPLICATIONS

The present application is the national stage entry of International Patent Application No. PCT/EP2016/070882, filed on Sep. 5, 2016, and claims priority to Application No. EP 15185785.1, filed in on Sep. 18, 2015, the disclosures of which are expressly incorporated herein in entirety by reference thereto.

TECHNICAL FIELD

The present disclosure relates to the field of drug delivery devices and in particular to the field of injection devices for delivery of a liquid medicament by way of injection.

BACKGROUND

Drug delivery devices for setting and dispensing a single or multiple doses of a liquid medicament are as such well-known in the art. Generally, such devices have substantially a similar purpose as that of an ordinary syringe.

Drug delivery devices and in particular injection devices have to meet a number of user-specific requirements. For instance, with patient's suffering chronic diseases, such like diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easy understandable. Moreover, a dose setting as well as a dose dispensing procedure must be easy to operate and has to be unambiguous.

The medicament to be dispensed by the drug delivery device is provided and contained in a multi-dose cartridge. Such cartridges typically comprise a vitreous barrel sealed in distal direction by means of a pierceable seal and being further sealed in proximal direction by the piston. With reusable drug delivery devices an empty cartridge is replaceable by a new one. In contrast to that, drug delivery devices of disposable type are to be entirely discarded when the cartridge is empty.

Automated medicament delivery devices, such like auto-injectors provide a rather easy and convenient approach to inject a predefined dose of a liquid medicament into biological tissue.

With some automatically or semi-automatically driven drug delivery or injection devices it is hence convenient to connect a suction pump to a distal outlet of the cartridge whereas the proximal end of the cartridge is sealed by the piston. Extraction and withdrawal of the medicament due to a suction effect of the suction pump is then typically accompanied by a distally-directed but suction-based displacement of the piston relative to the barrel.

Delivery devices equipped with an electric drive and hence with an electrically-operated pump are typically configured as a reusable device allowing to replace an empty cartridge by a new one. Such electrical pump-driven devices comprise at least a reusable unit to be connected with a disposable unit, wherein the cartridge is typically located inside the disposable unit. Upon deploying the device and prior to extract an initial dose from a new cartridge the cartridge has to be mounted inside the drug delivery device or the disposable device unit has to be connected with the reusable device unit. In either case the time interval between a manufacturing and filling of a cartridge and an initial use of the cartridge by means of the drug delivery device or injection device may be comparatively long. At least some days, weeks, months or even years may have passed from the manufacturing of the cartridge and its initial use in or with a suitable drug delivery device.

Depending on a storage time or the shelf life of a cartridge a breakaway or break-loose force to be applied onto the piston may be substantially high for driving the piston in distal direction relative to the barrel of the cartridge. Therefore, the suction force of a pump to be used with such a cartridge in connection with such drug delivery devices needs to be quite large. This requires implementation of rather large and powerful pumps and requires implementation of tubes or comparable fluid-guiding structures that are capable to transfer and to withstand such comparatively large suction forces.

The implementation of rather large, powerful and also heavy weight pumps in drug delivery devices is of particular disadvantage when the drug delivery device is intended for a mobile use, where weight, space and storage of electric energy are of particular relevance.

It is therefore an object of the present disclosure to provide an improved drug delivery device for dispensing of a liquid medicament, typically by way of injection. The drug delivery device or the injection device should provide an effective and simple means to overcome an initial breakaway force or break-loose force necessary to displace a piston inside a barrel of a cartridge after the piston has been subject to a short-term or long-term storage prior to its use in the drug delivery device. The improvements to be made to the drug delivery device should be rather simple and cost-efficient and should be easy to implement into existing designs of drug delivery devices. Optionally, the improvements to be made to the drug delivery device should be suitable for retrofitting of existing drug delivery devices.

SUMMARY DISCLOSURE

In one aspect the disclosure relates to a drug delivery device for dispensing of a liquid medicament. The disclosure particularly relates to an injection device that provides dispensing of a single or multiple well-defined doses of a liquid medicament and further provides injection of the liquid medicament into biological tissue of a patient. The drug delivery device comprises a housing to accommodate a cartridge filled with the liquid medicament. The cartridge to be assembled in the housing has a piston slidably displaced inside the cartridge, wherein said piston seals a proximal end of the cartridge. Typically, an opposite end, hence a distal end of the cartridge comprises or forms an outlet through which the liquid medicament can be extracted from the interior of the cartridge.

In addition, the drug delivery device comprises at least one resilient member having a first end that is arranged at an inside-facing sidewall portion of the housing. The resilient member further has a second end opposite to the first end. The second end is configured to abut with or to abut against the piston of the cartridge. In particular, the second end of the resilient member is configured to abut with a proximally-facing surface of the piston so as to exert a pressure onto the piston that acts in distal direction.

By means of the at least one resilient member typically sandwiched between an inside-facing sidewall portion of the housing and the piston of the cartridge, the piston can be somewhat pre-tensed in distal direction. With a suction-based withdrawal or extraction of the medicament from the cartridge via its distal outlet the resilient member supports an initial displacement of the piston relative to the cartridge, hence, relative to a tubular-shaped barrel of the cartridge in which the piston is slidably arranged.

Investigations have revealed that a first or an initial displacement of the piston inside the cartridge after long-term or even short-term storage of the cartridge requires an initial force level that is much larger than a force level normally to be applied to a non-moving piston at the beginning of frequent dispensing procedures. In typical application scenarios the piston might be subject to a single continuous displacement for emptying the cartridge in one go. In such a scenario the cartridge is only subject to dynamic friction after it has set in motion initially. In other typical scenarios of use the medicament is dispensed or injected in accordance with a predefined administering schedule according to which several doses of the medicament are dispensed and extracted from the cartridge at consecutive times, wherein the time intervals between consecutive dispensing procedures are rather small compared to the storage time between manufacturing of the cartridge and its initial use with the drug delivery device.

Hence, it is only at the very beginning and with an initial displacement of the piston inside the cartridge that a rather large force has to be applied to the piston in order to overcome the comparatively large break-loose or breakaway force of the piston relative to the barrel of the cartridge. A rather powerful pump for extracting the medicament from the cartridge would be only needed at the very beginning of the extraction of the medicament from the cartridge.

By means of the resilient member supporting an initial displacement of the piston relative to the barrel of the cartridge a very simple but rather effective means is provided to overcome the comparatively large breakaway or break-loose force of the piston. Consequently, the drug delivery device can be equipped with a less powerful pump that requires less assembly space, which comes along with a reduced weight and which is operable with reduced electrical power compared to conventional pump-driven drug delivery devices, where the suction force provided by the pump alone has to overcome the initial breakaway force of the piston inside the cartridge.

Accordingly, the resilient member configured to provide a well-defined force effect or pressure onto the piston of the cartridge in an initial configuration of the cartridge is of particular use to reduce the dimensions, the weight, the costs as well as the overall energy consumption of the drug delivery device.

According to another embodiment the resilient member is firmly attached to the sidewall portion of the housing with its first end. In this way the position of the resilient member inside the housing is rather fixed. Hence, the resilient member is inherently in a correct position inside the housing in order to engage and to abut with the piston of the cartridge as the piston is correctly arranged inside the housing of the drug delivery device. Generally, the resilient member is configured to get biased as the cartridge is assembled inside the drug delivery device. Hence, the longitudinal extension of the resilient member, hence its extension between the first end and the second end is selected such that in an unbiased or non-compressed configuration the axial or longitudinal extension of the resilient member is larger than a longitudinal or axial gap between a proximal end face of the piston and the inside-facing sidewall portion of the housing, to which the resilient member is attached.

In this way and upon correct assembly of the cartridge inside the housing the resilient member is at least partially biased or compressed in order to store mechanical energy. Depending on the degree of compression and the specific implementation and configuration of the resilient member, said member serves to exert a permanent force effect onto the proximal end face of the piston in order to support is displacement in distal direction relative to the barrel of the cartridge during an initial dispensing process.

According to another embodiment the resilient member protrudes substantially perpendicular from the sidewall portion. The second end of the resilient member furthermore extends into the interior of the housing. The second end of the resilient member protrudes into an area of the interior of the housing, which is typically occupied by the cartridge, in particular by its piston.

When in a final assembly configuration inside the housing the inside of the sidewall portion to which the resilient member is attached typically extends substantially parallel to the proximal face of the piston of the cartridge. Then and since the resilient member protrudes substantially perpendicular from the sidewall the resilient member with its second end also extends substantially perpendicular to the proximal end face of the piston. In this way, a force effect exerted by the resilient member towards and onto the piston is directed substantially parallel to the elongation of the piston. This is particularly beneficial for a smooth and longitudinal displacement of the piston inside the cartridge at the beginning of a first or initial dispensing procedure.

According to another embodiment the drug delivery device further comprises a pressure piece attached to the second end of the resilient member. The pressure piece is complementary-shaped to the cross-section of the piston. In a final assembly configuration it is intended that the pressure piece substantially covers the entire proximal face of the piston so as to exert a spatially homogeneous force effect onto the piston. By making use of a pressure piece, a punctual and spatially localized force provided by the resilient member can be evenly homogeneously distributed across the proximal end face of the piston.

In this way a rather homogeneous force effect acting on the piston can be provided, which is beneficial for a smooth displacement of the piston relative to the barrel of the cartridge at the beginning of an initial dispensing procedure. The pressure piece may be provided as a separate piece and may be detachably connected to the second end of the resilient member. Having the pressure piece replaceably assembled to the resilient member allows making use of different pressure pieces with one and the same resilient member. This allows reconfiguring the drug delivery device for a use of cartridges of different diameter. Alternatively and according to another embodiment the pressure piece and the resilient member are integrally formed. Then, the pressure piece actually forms the second end of the resilient member to get in direct axial abutment with the proximal face of the piston of the cartridge.

In another embodiment the resilient member is integrally formed with the sidewall portion of the housing. Typically, the sidewall portion of the housing or the entire housing is made of an injection-molded plastic material. By an integral formation of the resilient member and the sidewall portion a mutual assembly and a mutual attachment and fixing of resilient member and sidewall of the housing becomes somewhat superfluous. The integral and single piece embodiment of resilient member and sidewall portion of the housing is particularly suitable for a cost-efficient mass production of the drug delivery device. By integrally forming the resilient member with the sidewall portion of the housing any geometric tolerances with regard to the resilient member, the sidewall portion and their mutual assembly that would arise otherwise can be reduced to a minimum.

In another embodiment the resilient member comprises a compression spring. Here, a first longitudinal end of the compression spring is connected to the inside of the housing's sidewall portion whereas an opposite longitudinal end of the compression spring is configured to get either in direct or indirect axial abutment with the piston of the cartridge as the cartridge is correctly assembled inside the housing of the drug delivery device. As already mentioned, the distal end, hence the second end of the resilient member and hence the second end of the compression spring may be connected to a pressure piece having a geometric shape that commutates with the geometric shape of the proximal face of the piston of the cartridge. In typical embodiments the distal face of the pressure piece as well as the proximal face of the piston are substantially even or flat-shaped.

When implemented as a compression spring the resilient member may still be integrally formed with the sidewall portion or with the housing of the drug delivery device.

In another embodiment the resilient member is made of a plastic material, of an elastomeric material or of a combination thereof. Alternatively, it is also conceivable that the resilient member comprises a metal spring. When made of a plastic and/or an elastomeric material the resilient member is particularly light-weight and provides a well-defined elasticity in order to store mechanical energy when getting in abutment with the piston of the cartridge. By making use of a suitable plastic or elastomeric material a well-defined spring force or a well-defined elastic or resilient behavior of the resilient member in response to an axial compression between the piston of the cartridge and the sidewall of the housing can be provided.

According to a further embodiment the sidewall portion of the housing to which the resilient member is attached to is pivotably or detachably connected to the housing. A pivotable or detachable connection of the sidewall portion to the rest of the housing provides the possibility to insert the cartridge into the housing without any interference with the resilient member. With a pivotable embodiment the sidewall portion together with the resilient member attached thereto can be simply pivoted aside so as to give way for inserting the cartridge through an access opening of the housing into a respective cartridge compartment inside the housing.

Thereafter and by pivoting the sidewall portion together with the resilient member into a closed configuration the resilient member starts to exert a distally-directed pressure onto the piston of the cartridge. The same may be attainable with the sidewall portion of the housing being detachably connected to the housing. In either case the sidewall portion to which the resilient member is attached to can be fixed and interlocked to the housing, typically by way of various fastening members, such like mutually-corresponding positive locking members, such like clip fasteners or by means of a screwed connection.

According to a further embodiment the sidewall portion forms a lid to cover an access opening of the housing when said sidewall portion is pivotably connected to the housing. Then, one end of said lid is pivotably attached to the housing via a hinge while an opposite end of the lid comprises a fastener to releasably engage with a complementary-shaped fastening structure of the housing thereby keeping the lid in a closed configuration in which it closes the access opening. By making use of a hinged connection of the particular sidewall portion and the housing the lid formed by said sidewall portion is permanently connected to the housing and cannot get lost when in an open configuration, in which the access opening is accessible for insertion or replacement of a cartridge.

In another embodiment the drug delivery device further comprises a suction pump to connect to a distal end of the cartridge for a suction-based extraction of the liquid medicament therefrom. The pump may be configured as a peristaltic pump or other types of suction pumps by way of which the medicament can be withdrawn and extracted from the interior of the cartridge by way of suction. With a suction pump the drug delivery device does not require any drive mechanism operable to displace the piston of the cartridge actively, e.g. by way of providing a constant driving force from the proximal end to the piston for driving the same in a distal direction.

By means of a suction pump in combination with the resilient member a rather moderate suction effect can be applied to the liquid medicament while a comparatively large breakaway force of the piston is exerted only in combination with the force effect of the resilient member. Once the piston has at least slightly moved in distal direction at the very beginning of a dispensing procedure the cartridge is either subject to a continuous or stepwise emptying and extraction of its entire content. Since the time period for the complete emptying of the cartridge is rather small compared to a previous storage time of the cartridge any repeatedly arising static friction force between the sidewall of the cartridge's barrel and the piston slidably disposed therein will be substantially smaller and may be conquered exclusively by the suction effect arising from the pump of the drug delivery device.

In a further embodiment the drug delivery device also comprises a tube with a connector to establish a fluid transferring interconnection with the interior of the cartridge. The tube may be configured as a flexible tube and may belong to a disposable tube system mechanically interacting with, e.g. a peristaltic pump, such that through repeated squeezing of the flexible tube a well-defined amount of the medicament can be extracted from the interior of the cartridge by way of suction. The connector of the tube may be a standardized connector to connect to a complementary-shaped standardized connector at the distal outlet of the cartridge. Such standardized connector may be of male and female type e.g. of male and female Luer type.

It is also conceivable that the connector comprises a tipped cannula to pierced and to intersect a pierceable seal at the distal outlet of the cartridge. Typically, it is the proximal end of the tube that is provided with the connector to establish a fluid transferring interconnection with the cartridge's interior. Moreover, a distal end of the tube may be provided with a comparable connector. The distal end of the tube may be alternatively provided with an injection needle by way of which the medicament withdrawn from the cartridge can be directly dispensed and injected into biological tissue of a patient.

In another embodiment the drug delivery device is equipped with a cartridge filled with the medicament to be dispensed. The cartridge is firmly assembled inside the housing of the drug delivery device, in particular in a suitable cartridge compartment of the housing. When firmly assembled in a final assembly configuration inside the housing the piston of the cartridge is in axial abutment with the resilient member. Then, a level or a magnitude of a force exerted by the resilient member onto the piston is smaller than or substantially equal to a breakaway or break-loose force that is necessary to displace an initially resting piston relative to the barrel of the cartridge.

Typically, the cartridge is firmly assembled inside the housing, hence inside a particular cartridge compartment in a rather well-defined way, so that the piston, in particular its proximal end face is located in a well-defined axial position relative to the housing of the drug delivery device. It is either upon a correct assembly of the cartridge inside the drug delivery device or by closing a lid of the housing equipped with the at least one resilient member that a distally-directed pressure is permanently exerted onto the piston as long as the dispensing progress, hence the extraction or withdrawal of the medicament from the cartridge actually begins.

It is of particular use that the force level exerted by the resilient member is below the typical threshold of the initial breakaway or break-loose force so that the resilient member hardly influences the extraction or dispensing process. In addition and since the resilient member is typically attached to the inside of the housing of the drug delivery device the force exerted by the resilient member is only present during an initial stage of medicament extraction. As the piston of the cartridge moves in distal direction either continuously or stepwise the force effect of the resilient member will permanently decrease until the piston loses contact to the resilient member. Then the piston displacement is only and exclusively governed by the suction effect provided by the suction pump of the drug delivery device. As the piston and the resilient member lose mutual contact the level of the force provided by the resilient member abruptly drops to zero.

It is even also conceivable that the magnitude or level of the force exerted by the resilient member onto the piston is even larger than a breakaway or break-loose force that is necessary to displace the piston relative to the barrel. In this case the piston is at least slightly displaced in a distal direction upon a final assembly of the drug delivery device or upon insertion of the cartridge into the housing of the drug delivery device. The medicament located inside the cartridge may thus be slightly pressurized. This may help to fill the tube when the cartridge gets in fluid communication with the distally-located outlet end of the cartridge.

According to a further embodiment the housing of the drug delivery device comprises a reusable housing part and a disposable housing part, wherein the reusable housing part and the disposable housing part are detachably connectable. The disposable housing part may comprise all those components of the drug delivery device that are intended for a single use. Those components together with the disposable housing part are thus intended to be discarded after they have been used. The reusable housing part typically comprises those components of the drug delivery device that are intended for multiple uses. Typically, these are for instance the pump or at least an electric drive for driving the pump, an energy source, such like a battery and a control interacting with the drive and hence with the pump for extracting the medicament from the cartridge and for conducting the dispensing or injection process.

By splitting of the housing of the drug delivery device into a reusable part and into a disposable part a rather user friendly handling of the housing and hence of the entire drug delivery device can be provided. In a further embodiment the cartridge is assembled inside the disposable housing part. Upon emptying of the cartridge the disposable housing part is to be disconnected from the reusable housing part. It is then to be discarded together with the cartridge located therein. Typically, the disposable housing part also houses the tube or other components of the drug delivery device that get in direct contact with the liquid medicament or with the biological tissue of the patient. It is then rather practical and for the benefit of maintaining a high level of hygiene that the disposable housing part is intended to be discarded in its entirety.

In another embodiment the first end of the resilient member is attached to the reusable housing part or to the disposable housing part. When attached to the reusable housing part the resilient member may extend into the disposable housing part as the disposable housing part is attached to the reusable housing part. In this way the second end of the resilient member actually extends into the disposable housing part in which also the cartridge is located. In an alternative embodiment it is also conceivable, that the cartridge is not completely accommodated inside the disposable housing part but extends from the disposable housing part at least with its proximal end. Upon a final assembly of disposable and reusable housing parts the proximal end of the cartridge may then extend into a portion of the reusable housing part in which the resilient member is located.

In the present context the distal direction denotes a dispensing end of the drug delivery device. When the drug delivery device is implemented as an injection device the distal end of the drug delivery device faces towards an injection site of a patient. The proximal end or the proximal direction faces in the opposite longitudinal direction of the device. When implemented as an injection device, the proximal end of the drug delivery device is typically operable by a hand of a user so as to configure, to set and to conduct an injection procedure.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(02)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(02)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention as it is defined by the claims. Further, it is to be noted, that any reference numerals used in the appended claims are not to be construed as limiting the scope of the invention.

BRIEF DESCRIPTION OF THE FIGURES

In the following, an embodiment of the display arrangement, the drive mechanism and the drug delivery device is described in detail by making reference to the drawings, in which.

DETAILED DESCRIPTION

Figure 1:
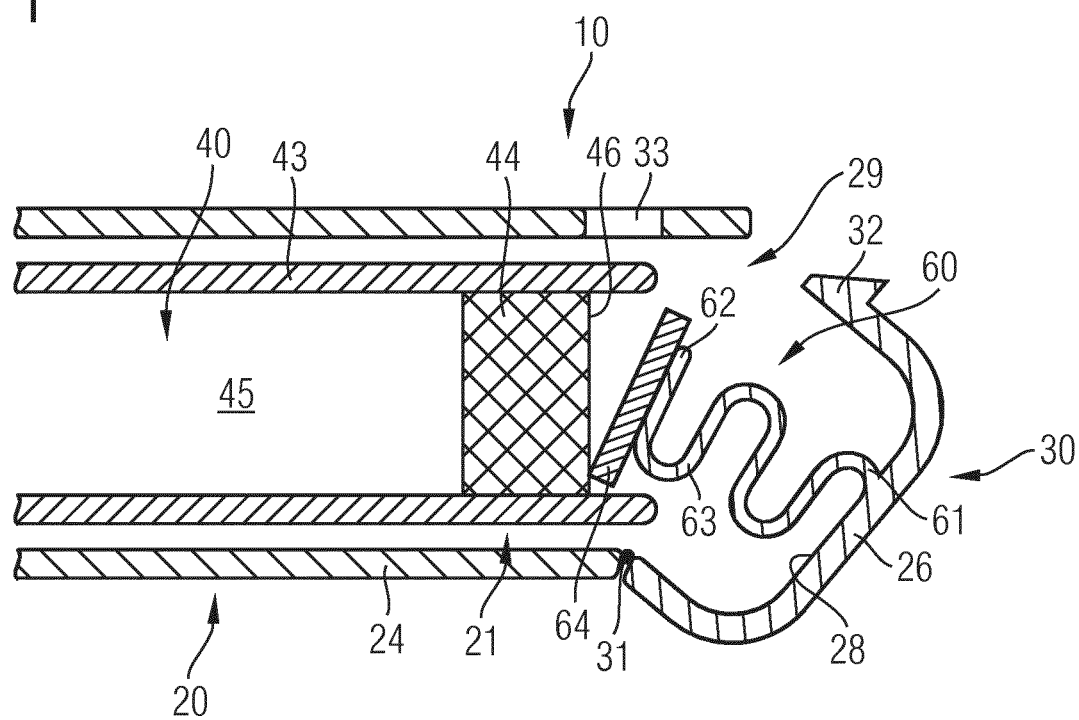
FIG. 1 shows a schematic illustration of a portion of the drug delivery device before the resilient member axially engages with the piston of the cartridge.
Figure 2:
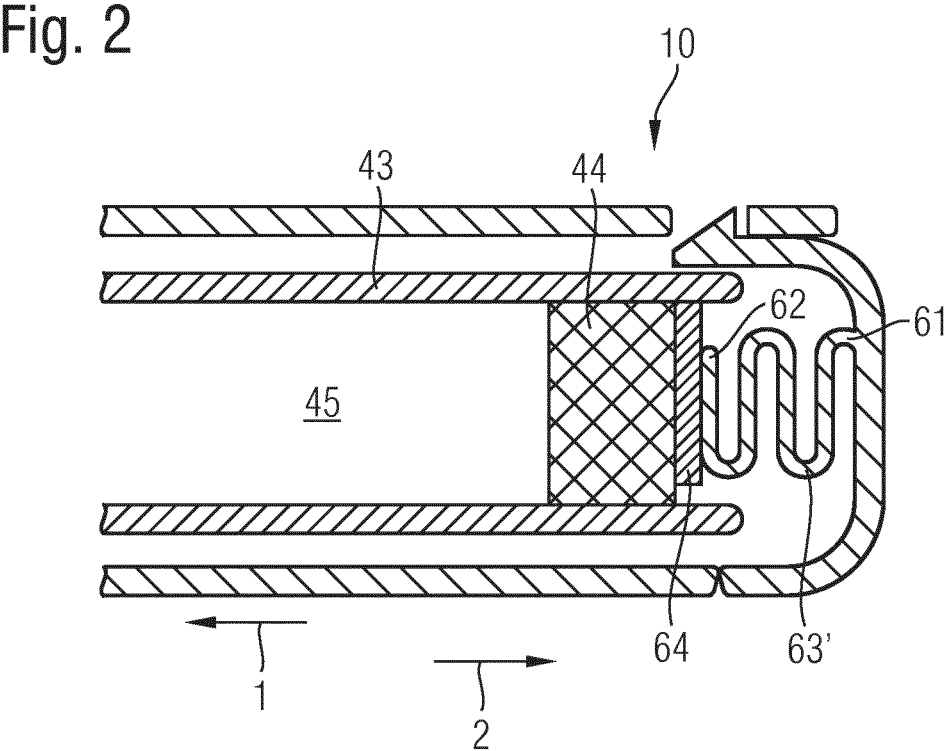
FIG. 2 shows the portion of the drug delivery device according to FIG. 1, wherein the cartridge and the housing of the drug delivery device are in a final assembly configuration in which the resilient member axially engages with the piston of the cartridge.
Figure 4:
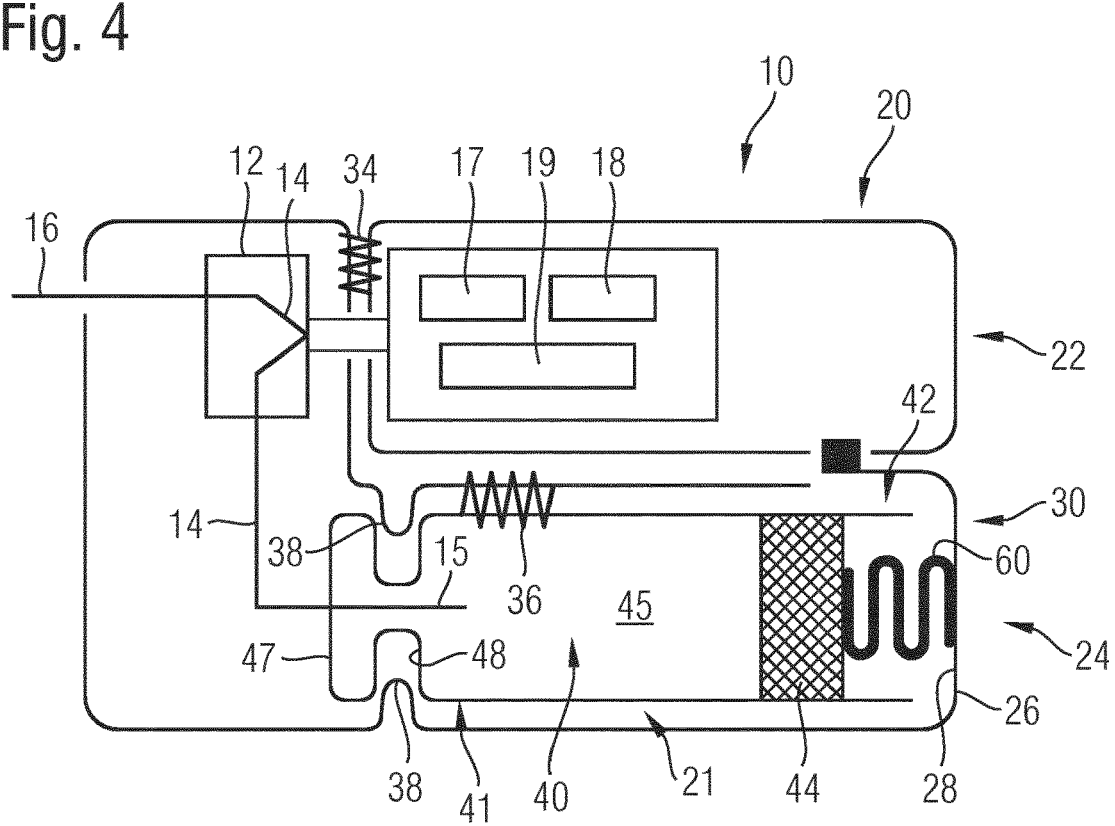
FIG. 4 shows a complete schematic illustration of the drug delivery device and FIG. 5 shows an alternative implementation of the drug delivery device.

The drug delivery device 10 as illustrated in FIGS. 1, 2 and 4 comprises a housing 20 having a reusable housing part 22 and a disposable housing part 24. The reusable housing part 22 and the disposable housing part 24 are detachably connected via fasteners 34, 36 by way of which the two housing parts 22, 24 can be detached and disconnected if required. The reusable housing part 22 accommodates various reusable components of the drug delivery device 10, such like an electric drive 17, a battery 18 as well as a control 19. The electric drive 17 is in mechanical interconnection with a pump 12, typically comprising a pump head by way of which a liquid medicament can be extracted and withdrawn from the interior 45 of a cartridge 40.

The pump 12 is connected to the interior 45 of the cartridge 40 by means of a tube 14 in a fluid-guiding way. The tube 14 may extend through the pump 12 and may be directly connected with a dispensing outlet 16. The tube 14 may be even integrally formed with the outlet 16. The dispensing outlet 16 may be configured as an injection needle by way of which the medicament transported through the tube 14 can be directly injected into biological tissue. Instead of a tipped cannula or an injection needle the dispensing outlet 16 may be also provided with a standardized connector by way of which the drug delivery device 10 is detachably connectable to a transfusion system or the like medicament transportation means.

Inside the disposable housing part 24 there is located a cartridge 40 comprising a tubular-shaped barrel 43 having a distal end 41 and having a proximal end 42. The cartridge 40, in particular its tubular shape defines a longitudinal or axial direction. At the distal end 41 the cartridge 40 comprises a pierceable seal 47 that is pierceable or penetrable by a connector 15 in fluid communication with the tube 14. The connector 15 may be firmly and non-moveably assembled inside the disposable housing part 24 while the cartridge 40 is insertable into the housing along a distal longitudinal direction, hence from the right to the left direction according to the illustration of FIG. 1, 2 or 4.

When arriving at a predefined position inside the disposable housing part 24 the cartridge 40 is firmly fastened inside the housing 20. An axial but also a radial fastening may be obtained by a mutual axial abutment of a cartridge's shoulder portion 48 getting in axial abutment with a correspondingly-shaped mount 38 at the inside of the housing part 24 of the housing 20 of the drug delivery device. In this way, the cartridge 40 can be firmly fixed inside the housing 20. The interaction of the mount 38 with the shoulder portion 48 at least delimits or confines a displacement of the cartridge 40 relative to the housing 20 in distal direction 1.

The housing 20 of the drug delivery device 10 further comprises a sidewall portion 26 with an inside 28 facing towards the proximal end 42 of the cartridge 40 when assembled inside the disposable housing portion 24. The sidewall portion may get in direct axial abutment with a proximal end of the cartridge, in particular with a proximal end 42 of its barrel 43. There is further provided a resilient member 60 which is configured as a type of a compression spring in the embodiment according to FIGS. 1, 2 and 4. The resilient member 60 comprises a first end 61 by way of which it is firmly attached to the inside 28 of the sidewall portion 26 of the housing 20 of the drug delivery device 10. With its opposite second end 62 the resilient member 60 points towards a proximal end face 46 of a piston 44 of the cartridge 40. The second end 62 therefore points into the interior 21 of the housing 20. The piston 44 serves as a proximal seal for the interior of the cartridge 45 filled with a liquid medicament. The piston 44 typically made of an elastic material is displaceable in longitudinal direction inside the tubular-shaped barrel 43 of the cartridge.

Optionally, the second end 62 of the resilient member 60 is provided with a pressure piece 64. In the present embodiment as shown in FIGS. 1 and 2 the pressure piece 64 is shaped as a flat disc that matches in contour and size with the proximal end face 47 of the piston 44. As it is apparent from a comparison of FIGS. 1 and 2 the sidewall portion 26 of the housing, in particular of the disposable housing part 24 is configured as a pivotable lid 30 that is pivotably attached to the disposable housing part 24 by means of a hinge 31.

The hinge 31, which may be configured as a film hinge, e.g. integrally formed with the sidewall portion 26, provides a permanent connection between the sidewall portion 26, hence of the lid 30 and the housing 20 of the drug delivery device 10. By pivoting the lid 30 in a clockwise direction as indicated in FIG. 1 an access opening 29 of the housing part 24 gets accessible for removal and for insertion of a cartridge 40 into a respective cartridge compartment inside the housing 20. Once a cartridge 40 has been correctly assembled inside the housing part 24 the lid 30 can be pivoted in a counter-clockwise direction so that a fastener 32 located at an end opposite to the hinge 31 can detachably or releasably engage with a correspondingly or complementary-shaped fastening structure 33 in a sidewall portion of the housing part 24.

This configuration is shown in FIG. 2. By closing the lid 30 the sidewall portion 26 approaches the proximal surface 46 of the piston 44 so that the pressure piece 64 gets in direct abutment with the piston 44. Upon a mutual engagement of the fastener 32 with the fastening structure 33 the resilient member 60 is subject to an axial compression. Hence, the windings 63 of the substantially unbiased or relaxed compression spring are subject to an axial compression. Consequently, the windings 63' as shown in FIG. 2 comprise a much smaller axial distance compared to the windings as illustrated in FIG. 1. In the fully assembled configuration as shown in FIG. 2 the resilient member 60 is compressed to a predefined degree and permanently exerts a distally-directed pressure onto the piston 44 of the cartridge 40.

Figure 3:
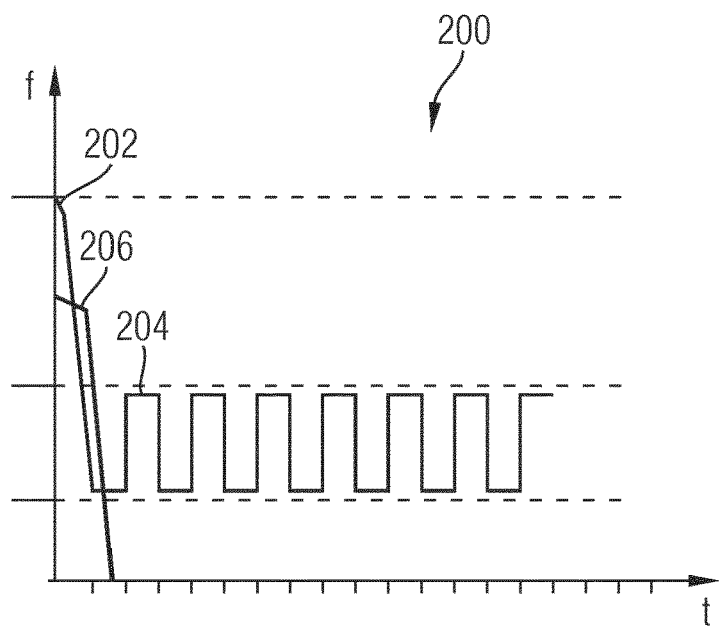
FIG. 3 shows a schematic diagram illustrating various force levels.

Typically, the level of the force effect provided by the biased or compressed resilient member 60 is substantially smaller, substantially equal to or even slightly larger than a force level 202 that is required for an initial breakaway of the piston 44 relative to the barrel 43 of the cartridge 40. In FIG. 3 a force level diagram 200 versus time is illustrated. In an initial configuration and after the cartridge 40 has been subject to a short term or long term storage a breakaway or break-loose force for setting the piston 40 in motion relative to the barrel 43 of the cartridge 40 is substantially high. This initial breakaway force 202 may be even higher than the force level 204 that is typically required during subsequent dose dispensing procedures for displacing the piston in distal direction.

In the diagram 200 according to FIG. 3 various consecutive dose dispensing procedures are illustrated as a kind of a rectangle or square function. Once the piston 44 has been in motion and has stopped at the end of a particular dispensing procedure a repeated displacement of the piston 44 inside the barrel 43 is accompanied by a substantially smaller level of a breakaway force as it is apparent from the consecutive peaks 204 in the diagram of FIG. 3.

In the diagram 200 of FIG. 3 there is further illustrated the force effect 206 that is provided by the resilient member 60. The initial force effect 206 at the beginning of a dispensing action may be fairly large. The level of the force effect provided by the resilient member 60 may be located between the force level 204 and the force level 202. But as the piston 44 is subject to a displacement in distal direction 1 the resilient member 60 is subject to expansion. Consequently, the force provided by the resilient member 60 decreases and even drops to zero when the piston 44 gets out of contact with the resilient member 60.

Even though the lid 30 has been shown to belong to a disposable housing portion 24 it is also implementable with a reusable housing part 22. Moreover, the resilient member 60 and its sandwiched configuration between a sidewall portion 26 of the housing 20 of the drug delivery device and a piston 44 of the cartridge 40 is universally implementable with a large variety of drug delivery devices and respective housings. The resilient member can be equally applied to reusable and disposable housing parts and respective drug delivery devices.

Figure 5:
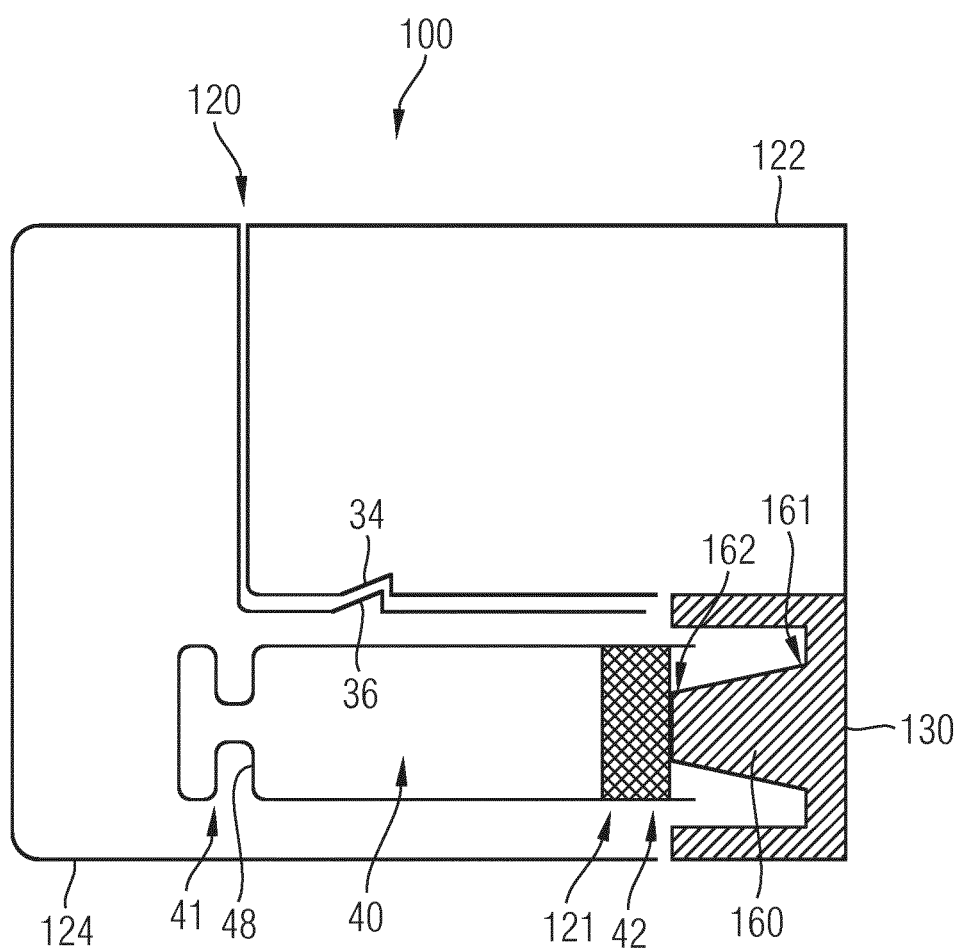

The embodiment according to FIG. 5 slightly differs from the embodiment as shown in FIG. 4. Also here, the drug delivery device 100 comprises a housing 120, wherein the housing 120 comprises a reusable housing part 122 and a disposable housing part 124. Even though not particularly illustrated the structure and configuration of the reusable housing part 122 is highly similar or even identical to that one of the reusable housing part 22 as shown in FIG. 4. The same is also valid for the components and the functionality of the disposable housing part 124.

The cartridge 40 can be assembled inside the disposable housing part 124 as described in connection with the embodiment as shown in FIG. 4. In the embodiment of FIG. 5, the cartridge 40 may be fixed with regard to the disposable housing part 124 in proximal direction 2 by means of a resilient member 160. Here and in contrast to the configuration according to FIG. 4 the resilient member 160 is implemented as a dome-shaped pin extending in distal direction 1 from the inside of a sidewall portion of a lid 130. Depending on the mutual interconnection of reusable housing part 122 and disposable housing part 124 the lid 130 may be rigidly connected to the reusable housing part 122.

It does not need to be pivotably attached thereto. The lid 130 may be configured as a protruding or flange-like housing portion extending from a sidewall of the reusable housing part 122. The mutually corresponding fasteners 34, 36 of the reusable housing part 122 and the disposable housing part 124 are configured such that upon reaching of a final assembly configuration the piston 44 of the cartridge 40 operably engages with the second end 162 of the resilient member 160. It does not only get in contact with the resilient member 160 but also serves to squeeze or compress the resilient member 160 in longitudinal or proximal direction so that the resilient member 160 is somewhat biased and resiliently compressed. The first end 161 of the resilient member 160 is firmly attached or fastened to the inside of the lid 130. The second end 162 therefore points into the interior 121 of the housing 120 and towards the proximal end face 46 of the piston 44. In this way the resilient member 160 generally provides a distally-directed pressure onto the piston 44 until an initial dispensing action takes place. In the embodiment according to FIG. 5 it is actually the resilient member 160 that is attached to the reusable housing part 122.

LIST OF REFERENCE NUMBERS 1 distal direction
2 proximal direction
10 drug delivery device
12 pump
14 tube
15 connector
16 dispensing outlet
17 drive
18 battery
19 control
20 housing
21 interior
22 reusable housing portion
24 disposable housing portion
26 sidewall portion
28 inside
29 access opening
30 lid
31 hinge
32 fastener
33 fastening structure
34 fastener
36 fastener
38 mount
40 cartridge
41 distal end
42 proximal end
43 barrel
44 piston
45 interior
46 proximal surface
47 pierceable seal
48 shoulder portion
60 resilient member
61 first end
62 second end
63 winding
64 pressure piece
100 drug delivery device
120 housing
121 interior
122 reusable housing part
124 disposable housing part
130 lid
160 resilient member
161 first end
162 second end

The invention claimed is:

1. A drug delivery device for dispensing of a liquid medicament, the drug delivery device comprising:
   a housing to accommodate a cartridge filled with the liquid medicament and having a piston slidably displaced inside the cartridge and sealing the cartridge;
   a resilient member having a first end arranged at an inside facing side wall portion of the housing and having a second end opposite to the first end to abut the piston of the cartridge; and
   an electronic suction pump to connect to a distal end of the cartridge for a suction-based extraction of the liquid medicament from the cartridge.

2. The drug delivery device according to claim 1, wherein the first end of the resilient member is firmly attached to the side wall portion of the housing.

3. The drug delivery device according to claim 1, wherein the resilient member protrudes substantially perpendicular from the side wall portion, and the second end extends into an interior of the housing.

4. The drug delivery device according to claim 1, further comprising a pressure piece attached to the second end of the resilient member, wherein the pressure piece is complementary shaped to a cross section of the piston.

5. The drug delivery device according to claim 1, wherein the resilient member is integrally formed with the side wall portion.

6. The drug delivery device according to claim 1, wherein the resilient member comprises a compression spring.

7. The drug delivery device according to claim 1, wherein the resilient member is made of a plastic material, an elastomeric material, or a combination thereof.

8. The drug delivery device according to claim 1, further comprising a tube with a connector to establish a fluid transferring interconnection with an interior of the cartridge.

9. The drug delivery device according to claim 1, further comprising the cartridge firmly assembled inside the housing with the piston axially abutting the resilient member, wherein a magnitude of a force exerted by the resilient member onto the piston is smaller than or substantially equal to a breakaway force necessary to displace the piston relative to a barrel of the cartridge when the piston is initially resting.

10. The drug delivery device according to claim 1, wherein the side wall portion of the housing is pivotably or detachably connected to another portion of the housing.

11. The drug delivery device according to claim 10, wherein:
the side wall portion forms a lid to cover an access opening of the housing,
a first end of the lid is pivotably attached to the other portion of the housing via a hinge, and
a second end of the lid comprises a fastener to releasably engage with a complementary shaped fastening structure of the housing when in a closed configuration in which the lid covers the access opening.

12. The drug delivery device according to claim 1, wherein the housing comprises a reusable housing part and a disposable housing part that are detachably connectable.

13. The drug delivery device according to claim 12, wherein the cartridge is assembled inside the disposable housing part.

14. The drug delivery device according to claim 12, wherein the first end of the resilient member is attached to the reusable housing part or to the disposable housing part.

15. A method of assembling a drug delivery device, the drug delivery device comprising a housing to accommodate a cartridge filled with the liquid medicament and having a piston slidably displaced inside the cartridge and sealing the cartridge, a resilient member having a first end arranged at an inside facing side wall portion of the housing and having a second end opposite to the first end to abut the piston of the cartridge, and an electronic suction pump to connect to a distal end of the cartridge for a suction-based extraction of the liquid medicament from the cartridge, the method comprising:
inserting the cartridge into an opening of the housing of the drug delivery device; and
placing a sidewall portion of the housing into a closed configuration to cover the opening and cause the second end of the resilient member of the drug delivery device to abut the piston of the cartridge.

16. The method of claim 15, wherein the sidewall portion comprises a pivotable lid, wherein placing the sidewall portion of the housing into the closed configuration comprises closing the lid to cover the opening and cause the resilient member of the drug delivery device to abut the piston of the cartridge.

17. The method of claim 15, wherein placing the sidewall portion of the housing into the closed configuration comprises causing the resilient member to exert a magnitude of force onto the piston smaller than or substantially equal to a breakaway force necessary to displace the piston relative to a barrel of the cartridge when the piston is initially resting.

18. The method of claim 15, wherein inserting the cartridge into the opening of the housing comprises placing the cartridge into fluid communication with a suction pump configured to deliver medicament from the cartridge.

19. The method of claim 15, wherein:
inserting the cartridge into the opening of the housing comprises inserting the cartridge into a disposable portion of the housing, and
the resilient member is arranged on the disposable portion or a reusable portion of the housing.

20. A drug delivery device for dispensing of a liquid medicament, the drug delivery device comprising:
a housing to accommodate a cartridge filled with the liquid medicament and having a piston slidably displaced inside the cartridge and sealing the cartridge;
a resilient member having a first end arranged at an inside facing side wall portion of the housing and having a second end opposite to the first end to abut the piston of the cartridge;
a suction pump to connect to a distal end of the cartridge for a suction-based extraction of the liquid medicament from the cartridge; and
a tube with a connector to establish a fluid transferring interconnection with an interior of the cartridge, wherein the tube extends through the suction pump and is connected to a dispensing outlet to allow the liquid medicament, transported through the tube, to be directly injected into a biological tissue.

\* \* \* \* \*

UNITED STATES PATENT AND TRADEMARK OFFICE
CERTIFICATE OF CORRECTION

| | | |
|---|---|---|
| PATENT NO. | : 11,298,458 B2 | Page 1 of 1 |
| APPLICATION NO. | : 15/760879 | |
| DATED | : April 12, 2022 | |
| INVENTOR(S) | : Andreas Bode | |

It is certified that error appears in the above-identified patent and that said Letters Patent is hereby corrected as shown below:

On the Title Page

Item (57) Column 2 (Abstract), Line 9, delete "(opposite" and insert -- opposite --

In the Specification

In Column 1, Line 9 (approx.), delete "in on" and insert -- on --

Signed and Sealed this
Twenty-seventh Day of December, 2022

Katherine Kelly Vidal
*Director of the United States Patent and Trademark Office*